US012649067B2

(12) United States Patent
Johnson et al.

(10) Patent No.: US 12,649,067 B2
(45) Date of Patent: Jun. 9, 2026

(54) ORAL CARE DEVICE AND METHOD

(71) Applicant: KONINKLIJKE PHILIPS N.V., Eindhoven (NL)

(72) Inventors: Mark Thomas Johnson, Arendonk (BE); Lutz Christian Gerhardt, Eindhoven (NL); Bart Gottenbos, Budel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 412 days.

(21) Appl. No.: 17/925,335

(22) PCT Filed: May 20, 2021

(86) PCT No.: PCT/EP2021/063408
§ 371 (c)(1),
(2) Date: Nov. 15, 2022

(87) PCT Pub. No.: WO2021/239555
PCT Pub. Date: Dec. 2, 2021

(65) Prior Publication Data
US 2023/0191143 A1 Jun. 22, 2023

(30) Foreign Application Priority Data
May 28, 2020 (EP) .................................... 20176970

(51) Int. Cl.
*A61N 1/40* (2006.01)
*A61C 17/22* (2006.01)
*A61C 17/34* (2006.01)

(52) U.S. Cl.
CPC .............. *A61N 1/40* (2013.01); *A61C 17/221* (2013.01); *A61C 17/3481* (2013.01)

(58) Field of Classification Search
CPC .......... A61N 1/40; A61N 1/306; A61N 1/322; A61N 1/205; A61N 1/26; A61N 1/0548;
(Continued)

(56) References Cited

U.S. PATENT DOCUMENTS 10,201,701 B2 * 2/2019 Levi ........................ A61C 17/32
10,231,811 B2 3/2019 Nahshon
(Continued)

FOREIGN PATENT DOCUMENTS

WO 2007121760 A1 11/2007
WO 2021239557 A1 12/2021

OTHER PUBLICATIONS

International Search Report and Written Opinion Dated Aug. 4, 2021 For International Application No. PCT/EP2021/063408 Filed May 20, 2021.
(Continued)

*Primary Examiner* — Katina N. Henson

(57) ABSTRACT

An oral care device has a field generator adapted to generate an electric field in a mouth of a user, responsive to an input control signal. The electric field is for imparting a force upon particles forming a biofilm to be removed by the oral care device or upon cleaning agent particles. A cyclic control signal is generated for intermittent generation of an electric field at a first RF frequency. The use of an intermittent generation of an RF electric field means the force applied to particles (in particular polarized particles) by the field is itself cyclic. The cyclic nature of this applied force is found to be more effective in the disintegration of a biofilm to be removed, and hence makes subsequent mechanical removal, e.g. by brushing, easier.

16 Claims, 6 Drawing Sheets

(58) Field of Classification Search
    CPC ....... A61C 17/32; A61C 19/06; A61C 17/221;
                                        A61C 17/3481
    USPC .......................................................... 15/22.2
    See application file for complete search history.

(56)                    References Cited

U.S. PATENT DOCUMENTS

2005/0064370 A1    3/2005  Duret
2006/0070195 A1*   4/2006  Morita ................. A61N 1/0548
                                                    604/20
2017/0027675 A1    2/2017  Nahshon
2018/0271630 A1*   9/2018  Wills ................. A61C 17/3418

OTHER PUBLICATIONS

"Dielectrophoresis as a Tool to Characterize and Differentiate
Isogenic Mutants of *Escherichia coli*", M. Castellarnau et al.,
Biophysical Journal vol. 91, Issue 10, Nov. 15, 2006, pp. 3937-
3945.

* cited by examiner

ORAL CARE DEVICE AND METHOD

This application is the U.S. National Phase application under 35 U.S.C. § 371 of International Application No. PCT/EP2021/063408, filed on May 20, 2021, which claims the benefit of EP Application Serial No. 20176970.0, filed May 28, 2020. These applications are hereby incorporated by reference herein.

FIELD OF THE INVENTION

The present invention relates to an oral care device and method, in particular a device for removing a biofilm from the mouth.

BACKGROUND OF THE INVENTION

It is known that radio-frequency (RF) electromagnetic emissions can be used to provide a cleaning function in the oral cavity. In particular, an oral cleaning device can include a cleaning unit, such as a head or mouthpiece portion, for insertion into an oral cavity of a user, which cleaning unit portion includes two or more electrodes coupled to an RF signal generator. The signal generator drives the electrodes with an RF signal which causes RF radiation to be emitted around and between the electrodes.

It is also known to deliver oral cleaning agent to the mouth as part of an oral care procedure.

U.S. Pat. No. 10,201,701 B2 describes a prior art electric toothbrush. The toothbrush comprises a platen, an RF generator, two RF electrodes, and a dielectric barrier situated between the two RF electrodes in the form of a silicone strip. The toothbrush also includes bristles. The dielectric barrier has a height which extends up to the level of the distal tips of the brush bristles. The barrier forces RF waves transmitted between the electrodes to travel over the top of the barrier, thus reaching the area where the bristles engage with the surfaces of the teeth and gums in use.

When the RF field interacts with surfaces of the teeth and gums, it provides a cleaning function by loosening the bonds between impurities and the surfaces in the mouth. In particular, RF fields generated in this way can remove dental plaque, and also dental calculus. Staining of teeth can also be reduced.

It is known that bio particles in a biofilm (e.g. plaque and calculus) to be removed, and indeed other polarizable particles such as cleaning agent particles as mentioned above, may be moved under the influence of a dielectrophoretic force. A given RF driving frequency will result in a force on the particles in a particular direction. This direction may however not remove plaque optimally, for example if it is towards the teeth or it may not result in a desired movement of the cleaning agent particles.

Plaque normally consists of bacterial micro-colonies embedded in an exopolysaccharide (EPS) matrix. In addition, it is known that dental biofilms such as plaque can show different degrees of tenacity making the biofilm difficult to remove. Plaque tenacity for example strongly differs by location. In areas that are easily reached by toothbrush bristles, e.g. the buccal and lingual tooth surfaces, plaque is hard to remove and the bristles need to apply sufficient work to be able to break and erode the plaque layers. Interproximally and subgingivally, e.g. in periodontal pockets, plaque is softer, but the bristles do not reach those areas, thus also not cleaning those. Such so-called hard-to-reach areas therefore require application of additional physical tools and principles to break and move the plaque away.

Therefore, there is a need to find means to more efficiently disintegrate the formed biofilms and/or to deliver a cleaning agent to the biofilms, thereby aiding the mechanical removal of the biofilms.

EP 3 104 807 discloses a teeth whitening device in which an AC activation signal is applied to regular toothpaste. An AC field is applied for example in the range 300 kHz to 40 MHz. The AC field may be continuous or pulsed.

SUMMARY OF THE INVENTION

The invention is defined by the claims.

According to examples in accordance with an aspect of the invention, there is provided an oral care device comprising:

a field generator adapted to generate an electric field in a mouth of a user, responsive to an input control signal;

a controller adapted to generate the input control signal, to control generation of the electric field, wherein the electric field is for imparting a force upon particles forming a biofilm to be removed by the oral care device or upon cleaning agent particles, wherein the controller is adapted to:

generate a cyclic control signal for intermittent generation of an electric field at a first RF frequency.

This device makes use of an intermittent generation of an RF electric field. In this way, the force applied to particles (in particular polarized particles) by the field is itself cyclic. The cyclic nature of this applied force is found to be more effective in the disintegration of a biofilm to be removed, either by direct interaction with the particles of the biofilm or by controlled delivery of cleaning agent particles or controlled interaction of cleaning agent particles with the biofilm. This makes subsequent mechanical removal, e.g. by brushing, easier.

The cleaning agent particles may comprise polarizable particles, or else one or more non-polarizable cleaning agent particles may be carried by a polarizable transport medium such as a capsule.

The cyclic control signal controls the timing of the generation of the RF field. Thus, the frequency of the cyclic control signal is much lower than the RF frequency itself.

The field generator creates a field with a certain field pattern within a space in the mouth, the field pattern dependent upon the control signal and upon the geometry of the field generator (e.g. the geometry or arrangement of electrodes or coils). The field pattern encompasses field strength gradients or field lines which, when acting upon polarizable particles, define a pattern of force paths through the space. The particles of the biofilm or the cleaning agent particles are electrically polarizable particles, and a force is applied to them depending on these field lines and gradients.

The controller is adapted to generate the cyclic control signal for the alternating generation of an electric field at said first RF frequency and at a second RF frequency.

Different RF frequencies result in different applied forces. The selection of these forces can be used to create an effective disintegration or else controlled movement or oscillation of cleaning agent particles.

There may be a switch between the first and second frequencies. Instead, the controller may be adapted to generate the cyclic control signal for generating a frequency sweep between said first RF frequency and said second RF frequency.

Thus, a switch or sweep of resulting forces and force directions can be generated.

The first RF frequency is for example below a threshold frequency and the second RF frequency is above the threshold frequency, thereby to generate dielectrophoretic forces on the particles in opposite directions. The dielectrophoretic effect is frequency-dependent, and in this way forces in opposing directions can be alternately applied. This provides an efficient disintegration solution.

The threshold frequency is for example 1 MHz, so that at least one frequency is below 1 MHz and at least one frequency is above 1 MHz.

The frequency of the cyclic control signal is for example in the range 0.1 Hz to 1 kHz, for example in the range 1 Hz to 100 Hz.

In an alternative set of examples (not within the scope of the claims), the controller may be adapted to generate the cyclic control signal for turning on and off the generation of an electric field at said first RF frequency. In this way, only a single frequency is used, but it is applied cyclically to alternate periods of force application using the RF electric field and periods of no force application.

In all examples, the oral care device may further comprise:
  a brush head; and
  a motor for driving the brush head with a vibratory motion with a vibration frequency.

This combines the disintegration of a biofilm (e.g. plaque) and/or the delivery of a cleaning agent with mechanical dislodging and removal.

The frequency of the cyclic control signal is for example equal to the vibration frequency or a sub-harmonic of the vibration frequency. In this way, forces are applied in opposite directions to the particles of the biofilm by combining the effects of mechanical vibration as well as electromagnetic forces from the RF field.

When the cyclic control involves on-off periods for a single RF frequency, when the RF field is turned on, a force may be generated in one direction, which supplements a force applied by the mechanical vibration. When the RF field is turned off, a force is still generated in the opposite direction by the mechanical vibration alone. In this way, a force with alternating direction is applied to the particles even with a single RF frequency.

This approach may also be used to generate a net force in one preferred direction. This may be used to guide cleaning agent particles to a desired location or a desired pattern of locations.

When the cyclic control involves two RF frequencies or a sweep of RF frequencies, positive and negative forces induced by the RF field may be enhanced by synchronization with the brush head vibration. For example, the force resulting from the RF field changes from positive to negative (i.e. changes direction) at the same moment that the brush head motion changes direction. With suitable synchronization, the force resulting from the RF field and that transmitted to the particle from the brush motion are always in the direction of brush head motion.

This driving scheme will be thus be even more efficient in vibrating and loosening the particles in the biofilm.

The vibration frequency is for example in the range 50 Hz to 1 kHz.

The field generator may be coupled to the brush head for moving with the brush head. A particle experiencing a force resulting from the RF field will for example be effectively captured by the force and move as the brush head moves.

The field generator is for example configured to generate a non-uniform electric field, having a field strength gradient in one or more directions, for generating a force on a polarizable particle along a direction of the gradient.

A non-uniform field such as this can be used to move electrically polarized particles. A polarized or polarizable particle will move along the direction of the field strength gradient due to the non-uniform force experienced at each pole of the particle's electric dipole. Thus, the field can be configured so as to exhibit field strength gradients which define one or more gradient paths corresponding to directions in which forces are desired to be applied. The non-uniform electric field can be used to move electrically polarizable or polarized particles by means of the dielectrophoresis (DEP) effect.

Forces may be exerted on particles of the biofilm to be removed in this way, but also forces may be applied to cleaning agent particles which are delivered to the mouth cavity. Thus, the field can be configured so as to exhibit field strength gradients which define one or more gradient paths leading toward locations where those cleaning agent particles are desired to be delivered.

In this case, the system may use electrically polarizable capsules having oral treatment agents contained therein, the electrically polarizable capsules constituting the cleaning agent particles susceptible to the field. These capsules can be moved by means of the non-uniform electric field to the desired locations in the mouth. The active agent therein may then be deployed at those locations. This might happen without further interaction from the device, e.g. the capsules are water soluble and break down due to interaction with saliva, or it may be triggered by an activation stimulus generated by the device.

The field generator for example comprises one or more conductive elements, electrically coupled to the controller, and the control signal is an electrical drive signal for electrifying the one or more conductive elements.

The oral care device is for example controlled by a method comprising:
  generating a control signal, to control generation of an electric field in the mouth of a user, wherein the electric field is for imparting a force upon particles forming a biofilm to be removed by the oral care device or upon cleaning agent particles,
  wherein the control signal comprises a cyclic control signal for the alternating generation of an electric field at a first RF frequency and at a second RF frequency, wherein the cyclic control signal is for:
  generating a frequency switch between said first RF frequency and said second RF frequency; or
  generating a frequency sweep between said first RF frequency and said second RF frequency.

The invention also provides a computer program product comprising computer program code, the computer program code being executable on a processor or computer. When the processor or computer is operatively coupled with a field generator, the code is configured to cause the processor to perform the method defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
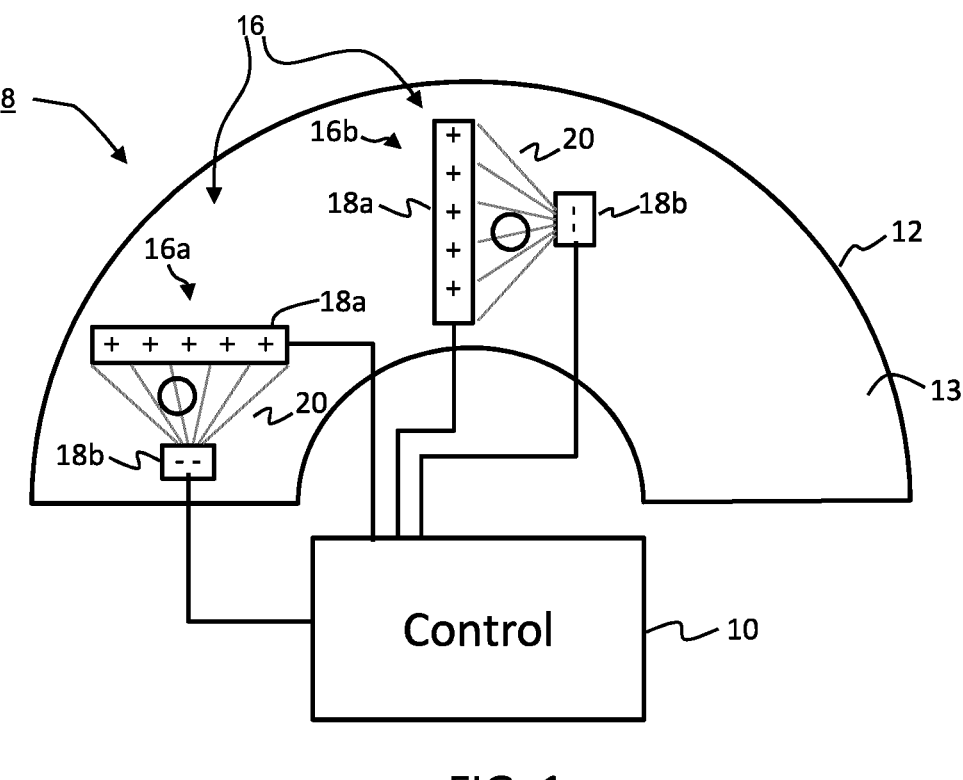
FIG. 1 schematically illustrates components of a first example device.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an oral care device which has a field generator for generating an electric field in a mouth of a user, responsive to an input control signal. The electric field is for imparting a force upon particles forming a biofilm to be removed by the oral care device or cleaning particles. A cyclic control signal is generated for an intermittent generation of an electric field at a first RF frequency (i.e. the first frequency is applied with a duty cycle, with periods when the RF field is generated at that frequency, and periods when there is a different frequency RF field or no RF field). This means the force applied to particles is itself cyclic and thereby more effective in the disintegration of a biofilm to be removed.

The invention thus relates to the use of forces induced by an RF field to assist in the loosening of a biofilm in the oral cavity either directly or by means of cleaning agent particles, thereby assisting removal of the biofilm. This application of an RF field may be used alone by the oral care device (e.g. it may be a purely RF treatment device or it may be followed by conventional brushing), or else the oral care device may implement the combination with physical brushing. For example the RF based oral care device may be integrated into an electric toothbrush or a mouthpiece brushing device. The oral care device may also be used in combination with the delivery of an oral treatment substance for example active agents such as fluoride, whitening solutions, mouthwash and specialized toothpaste, or a gel.

The invention relates in particular to the control of the forces resulting from the use of an RF field to act on biofilm particles or to control movement of cleaning agent particles. The other functions of the oral care device, such as electric brushing will not therefore be described in detail.

FIG. 1 schematically illustrates components of a first example device according to one or more embodiments.

The device 8 comprises a field generator 16 adapted to generate a first electric field 20 in a space responsive to an input control signal.

The device further includes a controller 10 adapted to generate the control signal, to control generation of the electric field 20 in the space. The field is for imparting a force upon particles of a biofilm, or other polarizable particles such as cleaning agent particles, susceptible to the field.

The field generator 16 is for operation in a mouth of a user. When the field is to apply a force to particles of the biofilm itself, the direction of the force applied to the particles of the biofilm preferably includes at least a component which is non-normal to the tooth surface, thereby providing a lateral force.

In this example, the field generator comprises two field generation arrangements or portions 16a, 16b, each comprising a first 18a and second 18b conductive body which are arranged to receive the control signal from the controller 10. Each generates a respective local field 20 between the respective conductive bodies, for applying forces to particles in a local area. However, this is not essential and in other examples, a single field generation arrangement could be provided, arranged to generate a field over a single area.

In this example, the device 8 comprises a support body 12 which carries or integrates the field generator 16a, 16b. For example, the field generator is carried on a support surface 13 of the support body or is integrated beneath the support surface. The controller 10 may also be carried by or integrated in the support body 12, or it may be separate from the support body and electrically coupled or coupleable with the field generator 16 of the support body. For example, in some cases, the device 8 may further comprise a handle or body portion to which the support body 12 couples or attaches, and which integrates the controller 10.

In the example illustrated in FIG. 1, each field generation arrangement 16a, 16b of the field generator 16 comprises a respective pair of electrodes 18a, 18b, separated by a space, and arranged to receive a voltage supply from the controller 10 causing charging of the electrodes. This induces an electric field 20 between the electrodes.

When the field 20 is generated by the field generator 16, the particles susceptible to the field have a force applied to them.

There are different options for the form and structure of the device 8 depending upon the application. For example, the invention can be implemented in a range of different oral care devices such as mouthpiece devices, toothbrushes, interdental cleaning devices, flossing devices, and oral irrigator devices.

FIG. 1 shows one example in the form a mouthpiece device having an arcuate support body 12 with a support surface 13. The arcuate shape permits the mouthpiece to be received in an oral cavity of the user. It may be shaped to conform to the geometry or contours of a user's mouth (e.g. a specific user or a typical user). It may have upper and lower surfaces. The conductive elements of the field generator 16 may be carried by the support surface 13 of the support body 12.

As explained in more detail below, the control signal generated by the controller 10 is dynamically varied as a function of time, to dynamically control a force exerted on the susceptible particles. The control signal may be varied over time to dynamically control the way particles in the generated electric field are polarized. In particular, the polarization is dependent on frequency. The frequency can for example be controlled to cause the force to change in magnitude and sign. The field generator 16 is thereby configured to generate a non-uniform field 20 (non-uniform field strength) having a field strength gradient in one or more directions, for apply a force to the particles along a direction of the gradient.

A non-uniform field such as this can apply a force to electrically polarizable or polarized particles. A polarized particle will have a force applied along the direction of the field strength gradient due to the non-uniform force experienced at each pole of the particle's electric dipole. A non-uniform electric field can in this way be used to apply a force to electrically polarizable or polarized particles by means of the dielectrophoresis (DEP) effect.

In the example of FIG. 1, to facilitate the non-uniform electric field 20, the electrodes 18 of each pair differ in respective size. This is just one way to create a non-uniform field pattern. For example, the first electrode 18a in FIG. 1 is longer than the second electrode. It may be longer in a dimension perpendicular the direction of the separation between the pair of electrodes for example.

Thus, an asymmetric pair of electrodes is provided. By providing one electrode 18a which spans a larger distance than the other 18b along a direction perpendicular their separation, this results in a field which is more spatially spread on one side of the separation space than the other, with the result that there is a net force toward the smaller electrode.

More generally, each electrode 18a, 18b of the pair may have a respective electrically chargeable or active area for generating the electric field 20 in the space between the pair when electrically charged, and wherein the electrically chargeable or active areas of the two electrodes may differ in size. Thus the parts of the electrodes 18a, 18b which become charged and contribute to the field may differ in area between the electrodes. They may additionally or alternatively differ in dimensional extension along a direction perpendicular to a direction of the separation between the electrodes.

It is noted that providing electrodes of different lengths or areas is not the only way to create a spatially non-uniform field. An alternative means for instance is to provide a pair of electrodes of the same length, spaced from one another, but disposed at an oblique angle with respect to one another. More generally, any electrode arrangement can be used in which the potential gradient between the electrodes varies spatially, rather than a simple parallel plate arrangement which generates a uniform field.

The electrodes may be plate electrodes, but equally one of the electrodes of each pair of electrodes may be a flat plate electrode, and the other electrode may have a different, round-ended shape, so that its electrically active area extends around side surfaces of the electrode.

Figure 2:
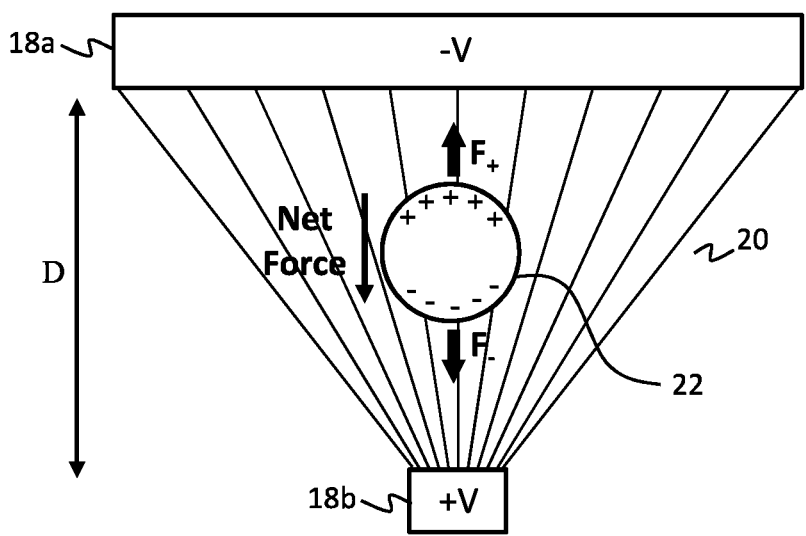
FIG. 2 shows an example pair of electrodes for inducing an electric field between them, for implementing a dielectrophoresis (DEP) effect.

The DEP effect is illustrated in FIG. 2, which shows an example pair of electrodes 18a, 18b, separated by a space, D. One electrode 18a is negatively charged, the other 18b is positively charged, thereby inducing an electric field between them. The first electrode 18a is longer than the second 18b in a dimension perpendicular the direction of separation, D, between the electrodes. This has the effect that for a polarized or polarizable particle 22 located within the field, there is a net force on the particle toward the smaller electrode 18b, along the direction of separation between the electrodes. This is because in the non-uniform field, the particle is not uniformly polarized, since different parts of the particle are in field regions of differing field strength.

Where the particle is an electrically polarizable particle, and the pair of electrodes is driven with an alternating potential to create an alternating field, this effect is known as the dielectrophoresis (DEP) effect.

In this effect, the electric field 20 polarizes the particle 22, so that the poles experience a force along the field lines, which can be either attractive or repulsive according to the orientation on the dipole. Since the field 20 is non-uniform, and at this frequency the particle polarizes in phase with the RF field (positive DEP) the pole experiencing the greatest electric field will dominate over the other, and the particle will move in that direction. At other frequencies where there is negative DEP, the particle will of course move in the opposite direction.

Bio particles in the biofilm or other polarizable particles such as cleaning agent particles may have a force applied and hence move (if and when they are free to do so) under the influence of this dielectrophoretic force. However if a single RF driving frequency is used the force on the particles is always in the same direction. If this direction is for example towards the teeth, it will not remove plaque optimally.

Plaque normally consists of bacterial micro-colonies embedded in an exopolysaccharide (EPS) matrix. In addition, it is known that dental biofilms or plaque can show different degrees of tenacity making the biofilm difficult to remove. Therefore, there is a need to find means to more efficiently disintegrate the formed biofilm aiding the mechanical removal of biofilm.

Plaque tenacity strongly differs by location. In areas that are easily reached by the toothbrush bristles, e.g. the buccal and lingual tooth surfaces, plaque is hard to remove and the bristles need to apply sufficient work to be able to break and erode the plaque layers. Interproximally and subgingivally, e.g. in periodontal pockets, plaque is softer, but the bristles do not reach those areas, thus also not cleaning those areas. Such so-called hard-to-reach areas therefore require application of additional physical tools and principles to break and move the plaque away.

Figure 3:
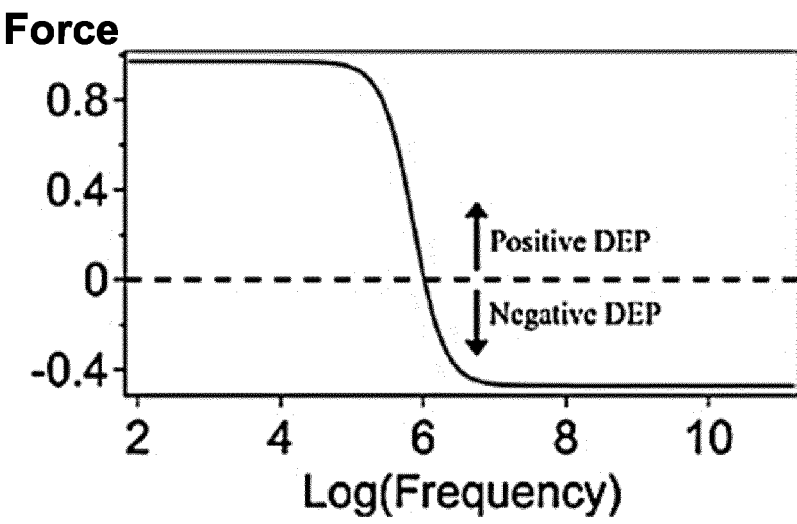
FIG. 3 shows the force in a particular direction versus a logarithmic frequency.

It is known that the net dielectrophoretic force can be changed in direction depending upon the frequency. This is illustrated in FIG. 3, showing the force in a particular direction (y-axis, arbitrary units) versus a logarithmic frequency (x-axis, Hz). For typical biological cell like particles the switch occurs in the RF frequency range, for example around 1 MHz.

Reference is made to "Dielectrophoresis as a Tool to Characterize and Differentiate Isogenic Mutants of *Escherichia coli*", M. Castellarnau et. al., Biophysical Journal Volume 91, Issue 10, 15 Nov. 2006, Pages 3937-3945. This article shows that there in fact may be two crossovers of the dielectric force direction with respect to frequency for the bacteria investigated, and this may also apply to biofilms, which similarly comprise bacterial matter. These crossovers are termed transition frequencies, and they are different for different particle types, e.g. different bacteria.

The invention is based on the realization that these characteristics of the dielectrophoretic force can be exploited in an oral care device, such as a toothbrush, with RF field generation, to improve the movement of particles or the disintegration of a biofilm, for the cleaning of teeth or improving oral health.

The invention makes use of the intermittent generation of an electric field at least at a first RF frequency. There may also be combinations of RF frequencies, and these may optionally additionally be synchronized with the motion frequencies and amplitudes of an electric vibrating tooth brush head. One possible purpose is to facilitate removal of plaque by breaking connections between particles (cells or colonies) and EPS. Particles (cells or colonies) may additionally be moved out of hard-to-reach areas, e.g. out of periodontal pockets. Movement of cleaning agent particles may also be controlled.

The controller 10 for example provides an alternating drive signal between the electrodes 18a, 18b of each pair of electrodes, to thereby induce a (non-uniform) alternating field between each pair of electrodes. An RF field can be used to perform an oral cleaning function and/or it may be used to performing the function of guiding movement of the particles.

RF fields can be used for example with frequencies anywhere in the range of 10 kHz-100 MHz. A preferred frequency range may be 500 kHz-30 MHz. RF fields with frequencies in the order of 1 MHz, for example between 0.5 MHz and 1.5 MHz, have been found to be particularly effective in inducing movement of polarizable particles using the dielectrophoresis (DEP) effect.

Figure 4:
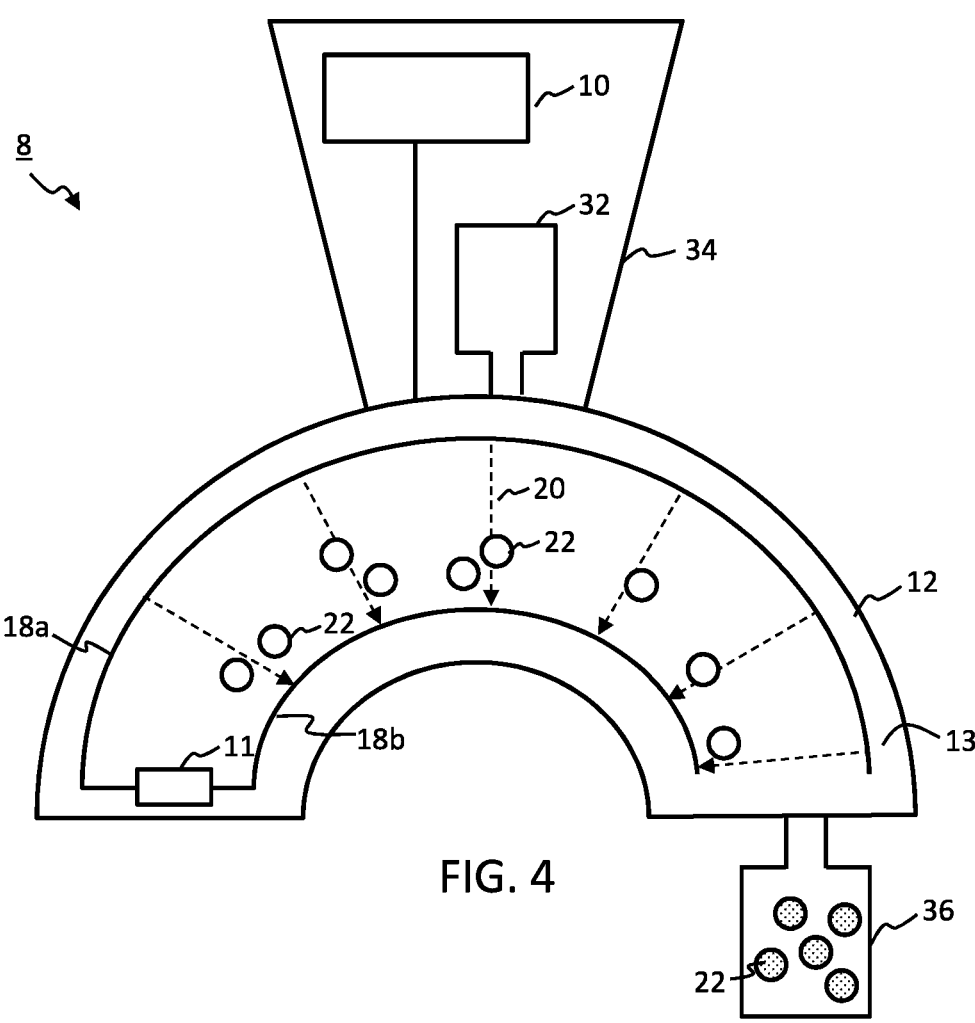
FIG. 4 shows in more detail a first example of oral care device.

FIG. 4 shows an example device in the form of a mouthpiece unit in more detail than the schematic example of FIG. 1.

The device again comprises a support body 12 having a support surface 13, the support body for being received in an oral cavity of a user. The support body is coupled to a handle portion 34 which houses the controller 10. The handle portion in this example is shown with the optional additional feature of a local reservoir 32 for holding cleaning agent particles including an active agent or substance for delivery in the mouth. It is fluidly connected to a deployment surface of the device, e.g. via one or more fluid passages, to enable particles to be received on the surface in use ready for delivery.

Additionally or alternatively, the device may be adapted to releasably couple or dock with an external reservoir 36, such as a bottle or other receptacle. When docked, particles can be loaded from the reservoir onto the support surface 13 ready to de delivered in the mouth.

In the example of FIG. 4, the device comprises a first 18a and second 18b arcuate electrode, the electrodes spaced from one another radially (along a radial dimension of the arcuate or semi-annular support body). The first electrode 18a extends proximal to, and follows the outline of, an outer circumferential edge of the body 12. The second electrode 18b extends proximal to and follows the outline of an inner circumferential edge of the body 12.

The two electrodes are connected to a voltage source 11, and supplied with opposing polarity voltages. An alternating voltage is used to generate an RF field.

A separate voltage source 11 and controller 10 are shown in FIG. 4. For example, the controller controls the drive scheme of the voltage source. However, in other examples, the controller 10 may provide the voltage source. The pair of electrodes 18a, 18b, in combination with the voltage source, provides a field generator 16.

When the electrodes 18a, 18b are driven with an AC voltage supply to generate the RF field in the manner explained in more detail below, electrically polarizable particles 22 can be driven to migrate along field gradient lines, e.g. toward the smaller, inner electrode 18b. The field gradient direction in this case is the radial direction, toward the second electrode, and the gradient is uniform along a circumferential direction. As a consequence, forces are directed towards the second electrode. Alternatively, forces can be applied to the static particles in the biofilm to be removed, thereby to disintegrate the biofilm.

Figure 5:
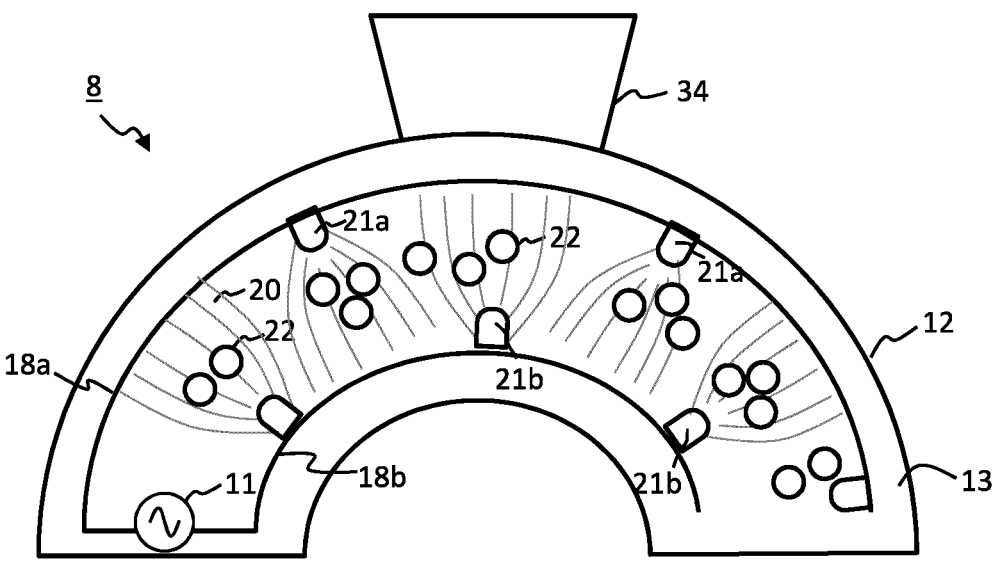
FIG. 5 shows in more detail a second example of oral care device.

FIG. 5 shows a further example oral cleaning device 8. This embodiment may be the same in all respects as that of FIG. 4 apart from the additional provision to each of the first 18a and second 18b electrodes of radially protruding electrode nodes 21. The first electrode 18a comprises a first set of nodes 21a, spaced along the length of the electrode, facing toward the second electrode 18b, and the second electrode 18b comprises a second set of nodes 21b, spaced apart and facing the first electrode. The first and second sets of nodes are circumferentially offset from one another, so that each node radially faces a node-free space on the other opposing electrode.

This pattern results in a non-uniform field, but wherein the field strength gradients guide particles toward the locations of the nodes 21a, 21b, Thus the nodes allow for defining different force directions, for example including a lateral component. Alternatively, more localized particle collection points may be defined across the support surface 13, permitting guidance of particles to more specific locations in the mouth when in use.

Figure 6:
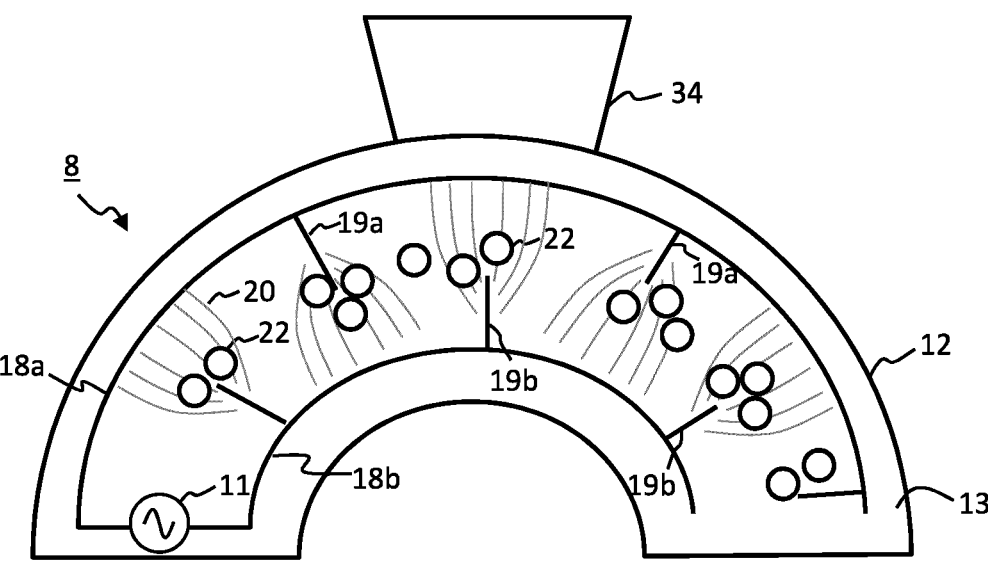
FIG. 6 shows in more detail a third example of oral care device.

FIG. 6 shows a further example oral cleaning device 8 which is again similar in all respects to the embodiment of FIGS. 4 and 5 apart from the configuration of the first and second electrodes. In this example, the first 18a and second 18b electrodes are provided in the form of arcuate interdigitated electrodes. The first 18a and second 18b electrodes each comprise a set of protruding electrode fingers 19a, 19b. These effectively perform the same function as the nodes 21 of FIG. 5, in providing more spatially defined particle collection points. When the electrodes 18a, 18b are driven with an alternating drive signal, to create an alternating field, the field strength gradients are directed toward the electrode fingers 19a, 19b.

As with the nodes of FIG. 5, the first electrode 18a comprises a first set of fingers 19a, spaced along the length of the electrode, facing toward the second electrode 18b, and the second electrode 18b comprises a second set of fingers 19b, spaced apart and facing the first electrode. The first and second sets of electrode fingers are circumferentially offset from one another, so that each finger radially faces a free space on the other opposing electrode.

The advantage of electrode fingers over nodes is that field strength gradients are directed toward their distal (free) ends, and the finger elements 19 can be made as long (in the radial direction) as desired. Thus it is possible to more flexibly define the force pattern (and for example the locations for particle collection).

Figure 7:
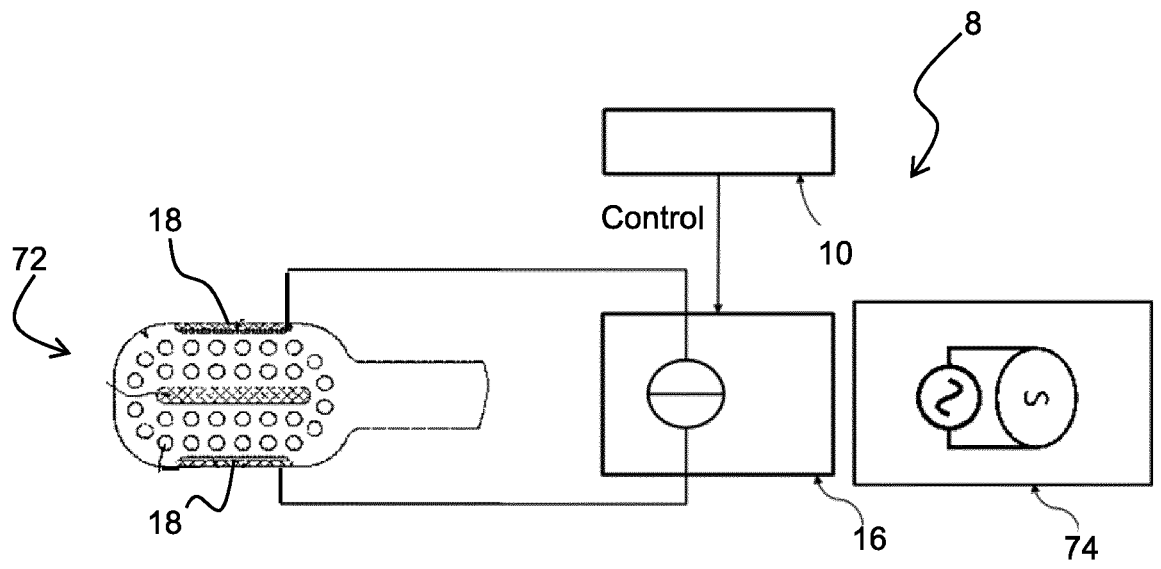
FIG. 7 shows the drive system for another example of an oral care device.

FIG. 7 shows an oral care device 8 in the form of a toothbrush and shows the RF field generator 16 and its controller 10 for generating the input control signal "Control", to control generation of the electric field by application to the electrodes 18. The electric field imparts a force upon particles forming a biofilm to be removed by the oral care device or on cleaning agent particles.

The oral care device in this example comprises an electric toothbrush with a brush head 72 and a motor and drive train 74 for driving the brush head with a vibratory motion with a vibration frequency. The controller 16 has suitable control electronics (such as a Schmitt trigger) to be able to switch at least between two different frequencies or to apply a duty cycle to a single frequency. In all cases, there will be a cyclic control signal for intermittent generation of an electric field of a first RF frequency, and this control signal may additionally control the generation at one or more further frequencies.

In a first example, the controller 16 applies two different frequencies of RF field, either side of the DEP switching point discussed above. Thus, the conventional RF driving scheme (of RF driving with a single frequency) is adapted to make better use of the DEP.

The RF electrodes in this example are driven using two RF frequencies, one each side of a threshold, which is a transition point between attraction and repelling of polarized or polarizable particles.

For example, the DEP driving force shown in FIG. 3 is explained above as having a transition frequency of around 1 MHz. Suitable driving frequencies may then be 0.5 MHz and 5 MHz, or 100 kHz and 10 MHz etc.

In addition to discrete frequencies, it is also possible to perform a frequency sweep between two extreme frequencies, if those extreme values again straddle the switching frequency between positive and negative DEP.

The switching between the frequencies should occur fairly rapidly, for example every few seconds or several times per second or even several hundred times per second, hence with a frequency between 0.1 Hz and 1 kHz.

This force direction reversal is of particular interest for applying force directly to the particles of the biofilm. As a consequence of this, the force on the bio particles of the biofilm in the mouth will reverse in direction at this switching frequency. The particles will thereby be vibrated and loosened more effectively than if the force is maintained in the same direction.

Since there are many different bacteria mixed in plaque having different sizes and properties, the transition frequencies between the bacteria will differ, as explained also in "Dielectrophoresis as a Tool to Characterize and Differentiate Isogenic Mutants of *Escherichia coli*" referenced above. When using a frequency sweep as discussed above, there are many occasions, particularly at frequencies around the transition frequencies of the specific bacterial species present, where one bacterium will be attracted, while the next bacterium will be repelled, pulling the plaque apart locally.

In a second example, the controller 16 applies only one frequency of RF field but with intermittent application of the field. Furthermore, the frequency of the cyclic control signal providing this intermittent field generation is preferably linked to the vibration in the brush, to make better use of the DEP.

Specifically, a single RF frequency may be used, but it is turned on and off with a period synchronized to the frequency (or a sub-harmonic of the frequency) of the brush head motion.

Figure 8:
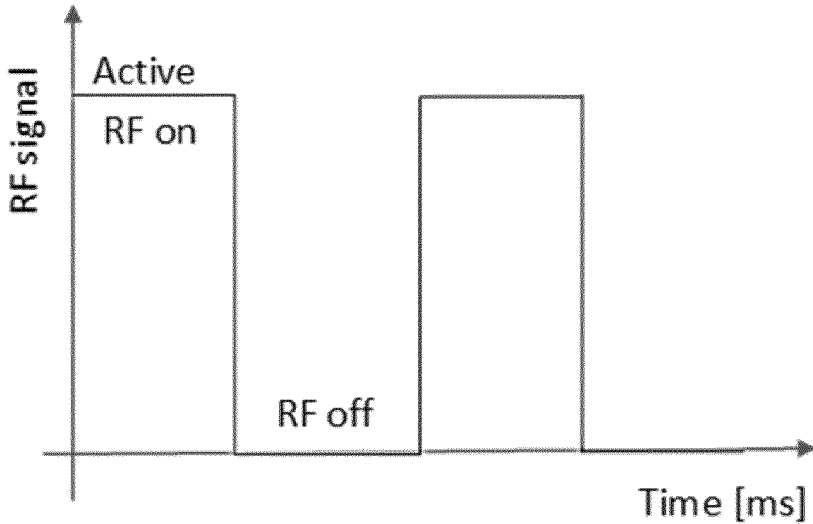
FIG. 8 shows a cyclic control signal for synchronization with a vibratory brush head motion.

FIG. 8 shows the cyclic control signal with a 50% duty cycle (as one possible example—other duty cycles may be used), and one period corresponds to one oscillation period of the vibratory brush head motion. While the RF field is activated, there is a force (the DEP force) on the polarizable particles, whilst when the duty cycle causes the RF field to de-activate this force is zero.

For systems which deploy cleaning agent particles, this may be used to control the movement of the particles. For example, as the brush vibrates, the RF field is displaced in space (following the brush motion, as the electrodes are mounted on the brush head). As a consequence, a particle experiencing a force (e.g. from the DEP) will be effectively captured by the force and move as the brush head moves.

If the RF is continuously active, this will cause some vibration (in the direction of the brush motion) but will not cause any net movement of the particles. However by applying this intermittent driving scheme, the particles may be captured and moved in one part of the duty cycle (where the brush head moves in one direction) but are released in the other (where the brush head moves in the opposite direction). As a consequence the particles may be repeatedly moved in the same direction instead of being moved backwards and forwards.

Figure 9:
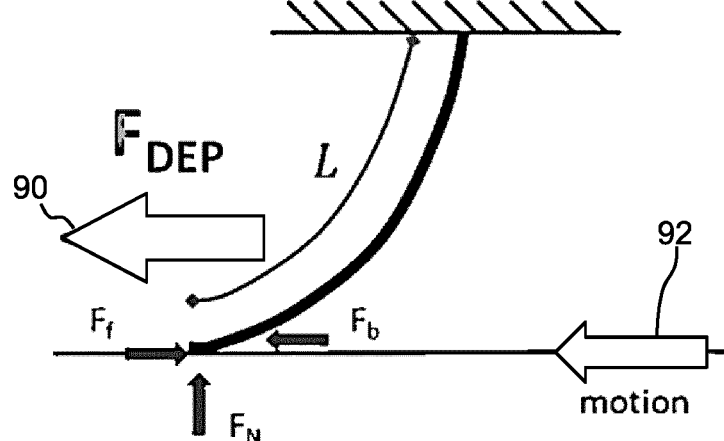
FIG. 9 shows a synchronized DEP force and direction of movement.

This situation is represented in FIG. 9. The DEP force resulting from the RF electric field is shown as arrow 90 and the direction of movement is shown as arrow 92, with the DEP force acting in the same direction as the brushing motion imparted by the vibration system. The bristle undergoes a bending and sliding motion. The reaction and friction forces are represented, these are of the order of mN.

Figure 10:
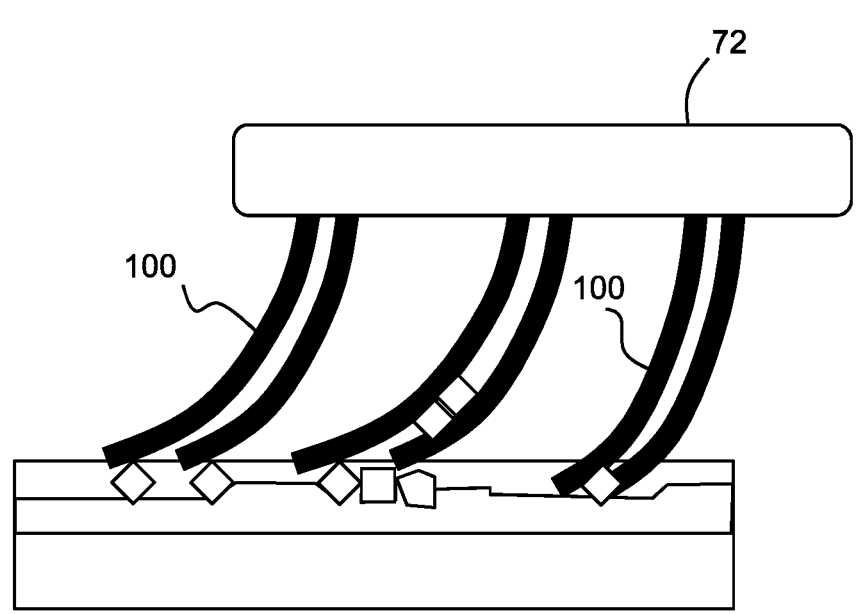
FIG. 10 shows a brush head with a set of bristles lifting particles in the manner represented in FIG. 6.

FIG. 10 shows a brush head 72 with a set of bristles 100, for moving particles in the manner represented in FIG. 9.

As the vibration frequency can be rather high (around a few 100 Hz) this results in very fast motion of particles in one direction. This can be particularly useful to remove bacteria out of subgingival areas, especially out of deeper periodontal pockets. Such pockets can be for example 5 mm deep, and bacteria are often loosely attached or even floating in the pocket fluid. In a specific pocket cleaning embodiment, the DEP force may be used to pull bacterial cells out of the pocket when synchronized with the brush sweep up.

Depending on the position and orientation of the brush (e.g. upper or lower jaw), the DEP force may be alternatively synchronized with the sweep down or the sweep up.

In a third example, the controller may implement a driving scheme with switching between two RF frequencies or applying a frequency sweep (as explained above for the first example), but synchronized with the vibration frequency of the brush (as explained above for the second example).

Thus, the known RF driving scheme is adapted to provide the cyclic control, but also in a manner to provide synchronization with the vibration in the brush to make better use of the DEP. The driving switches between at least two RF frequencies to induce positive and negative DEP at the frequency (or a sub-harmonic of the frequency) of the brush head motion.

The DEP force on the particles thereby changes from positive to negative at the same moment that the brush head motion changes direction. If this is correctly synchronized, the force of the DEP and also that transmitted to the captured particle from the brush motion are always in the direction of brush head motion.

Figure 11:
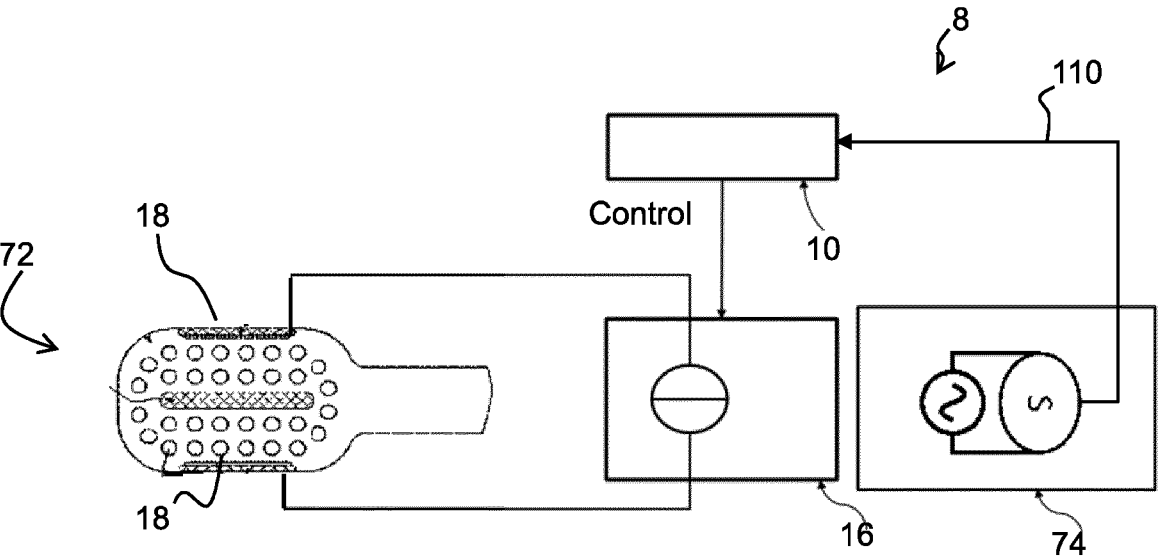
FIG. 11 shows a modification to the system of FIG. 7 to implement synchronization with the brush head vibration.

FIG. 11 shows the required modification to the system of FIG. 7. The drive train current or voltage or amplitude signal is used as synchronization and control signal 110 for the controller 10.

As explained above, the invention relates specifically to the control of the RF field and the forces that result, and these forces may be used to act directly on particles of the biofilm to disintegrate the biofilm, or they may be used to control the delivery of cleaning agent particles.

The cleaning agent particles for example comprise oral cleaning or treatment agents such as fluoride, whitening agents, mouthwash or antimicrobially effective particles.

The delivered agent can also include Catalytic Antimicrobial Robots (CARs) in a polarizable carrier capsule. These exploit iron oxide nanoparticles with catalytic functionality to (i) generate bactericidal free radicals, (ii) break down the biofilm exopolysaccharide (EPS) matrix, and (iii) remove the fragmented biofilm debris via electric field gradient—driven robotic assemblies in a controlled manner, preventing biofilm regrowth. Any other substance for an oral cleaning or treatment purpose can also be considered.

For most effective utilization of these agents, there is a need for homogeneous delivery of the agents across the regions of the mouth where they are required. For example, whitening agents need to be homogeneously spread across surfaces of the teeth, and antimicrobial particles need to be spread evenly across portions of the gums. However, delivering the agents to the parts of the mouth where they are needed is difficult and inefficient, which reduces their efficacy and causes inconvenience for a user.

The electric field may therefore additionally be used to manipulate the distribution of particles comprising oral treatment agents within the mouth.

The particles manipulated by the field may themselves be particles of an oral treatment agent, or may be carrier particles, which contain within them a treatment agent to be deployed. For example, the particles may be capsules for containing therein a treatment agent. The particles may then be guided to move due to a force induced on the particles by the field. For example, the particles may be guided to move along or across the surface 13 of the support body 12 in some cases to thereby transport them to the required location in the mouth.

The invention may be used in a system which only uses the RF for controlled delivery of cleaning agent particles. The invention may instead be used in a system which only uses the RF field for direct application of force to the particles of the biofilm.

In a system which implements both delivery of cleaning agent particles using the RF field and application of force to the biofilm itself using the RF field, the controller may then be selectively controllable between at least two different modes:

a particle delivery mode in which the controller supplies a control signal to the field generator for generating a field for guiding particles susceptible to the field to a desired location in the space; and a cleaning mode in which the controller supplies the intermittent control signal as described above to the field generator for generating an RF field in the space for performing an oral cleaning function. This may be performed at the same time as a vibratory brushing function.

The device may be configured with the functionality of triggering an activation of delivered particles. This activation may be a chemical or physical reaction process, or a process of breaking down particles to trigger release of their contents. This step may be performed subsequent to moving the particles to the desired locations in the mouth for example. Thus, the device may further comprise a particle activator adapted to generate a physical stimulus for stimulating an activation event of the agent particles. The particle activator is composed of the same or different components to the field generator. Thus, the particle activator may be provided by the field generator in some example, or may be a formed by a separate set of one or more components.

The stimulus may, by way of non-limiting example, include at least one of: a generated field (electrical and/or magnetic stimulus), a heat stimulus, and an acoustic stimulus.

Examples of a tooth brushing mouthpiece and an electric toothbrush are presented above. The invention may however also be applied in other oral cleaning devices such as irrigators or flossing devices.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. An oral care device comprising:

a field generator, comprising one or more conductive elements, and adapted to generate an electric field in a mouth of a user, responsive to an input control signal;

a controller adapted to generate the input control signal, to control generation of the electric field, wherein the electric field is for imparting a force upon particles forming a biofilm to be removed by the oral care device or upon cleaning agent particles, wherein the controller is adapted to generate a cyclic control signal for alternating generation of an electric field at a first RF frequency and at a second RF frequency, wherein the cyclic control signal is for:

generating a frequency switch between said first RF frequency and said second RF frequency; or generating a frequency sweep between said first RF frequency and said second RF frequency.

2. The oral care device of claim 1, wherein the first RF frequency is below a threshold frequency and the second RF frequency is above the threshold frequency, thereby to generate dielectrophoretic forces on the particles in opposite directions.

3. The oral care device of claim 2, wherein the threshold frequency is 1 MHz.

4. The oral care device of claim 1, wherein the frequency of cyclic control signal is in a range of 0.1 Hz to 1 kHz.

5. The oral care device of claim 1, further comprising:

a brush head; and a motor for driving the brush head with a vibratory motion with a vibration frequency.

6. The oral care device of claim 5, wherein the frequency of the cyclic control signal is equal to the vibration frequency or a sub-harmonic of the vibration frequency.

7. The oral care device of claim 6, wherein the vibration frequency is in a range of 50 Hz to 1 kHz.

8. The oral care device of claim 5, wherein the field generator is coupled to the brush head for movement with the brush head.

9. The oral care device of claim 1, wherein the field generator is configured to generate a non-uniform electric field, having a field strength gradient in one or more directions, for generating a force along a direction of the gradient.

10. The oral care device of claim 1, wherein the field generator comprises the one or more conductive elements, electrically coupled to the controller, and wherein the control signal is an electrical drive signal for electrifying the one or more conductive elements.

11. A non-transitory computer-readable medium storing a computer program which is executable on a processor operatively coupled with the field generator of the oral care device of claim 1, the program comprising instructions, which when executed by the processor, cause the processor to:

generate a control signal, to control generation of an electric field in the mouth of a user, wherein the electric field is for imparting a force upon particles forming a biofilm to be removed by the oral care device or upon cleaning agent particles, wherein the control signal comprises a cyclic control signal for alternating generation of an electric field at a first RF frequency and at a second RF frequency, wherein the cyclic control signal is for:

generate a frequency switch between said first RF frequency and said second RF frequency; or generate a frequency sweep between said first RF frequency and said second RF frequency.

12. The oral care device of claim 1, wherein the frequency of cyclic control signal is in a range of 1 Hz to 100 Hz.

13. An oral care device comprising:

a field generator, comprising one or more conductive elements, and adapted to generate an electric field in a mouth of a user, responsive to an input control signal; and a controller adapted to generate the input control signal, to control generation of the electric field, wherein the electric field is for imparting a force upon particles forming a biofilm to be removed by the oral care device, or upon cleaning agent particles, wherein the controller is adapted to generate a cyclic control signal for intermittent generation of an electric field at a first RF frequency, wherein the controller is adapted to generate the cyclic control signal for alternating generation of an electric field at said first RF frequency and at a second RF frequency.

14. The oral care device of claim 13, wherein the controller is adapted to:

generate the cyclic control signal for generating a frequency switch between said first RF frequency and said second RF frequency; or generate the cyclic control signal for generating a frequency sweep between said first RF frequency and said second RF frequency.

15. A method of controlling an oral care device, the method comprising:

generating a control signal, to control generation of an electric field in a mouth of a user, wherein the electric field is for imparting a force upon particles forming a biofilm to be removed by the oral care device or upon cleaning agent particles, wherein the control signal comprises a cyclic control signal for intermittent generation of the electric field at a first RF frequency;

generating a cyclic control signal for alternating generation of an electric field at a first RF frequency and at a second RF frequency, wherein the cyclic control signal is for:

generating a frequency switch between said first RF frequency and said second RF frequency; or generating a frequency sweep between said first RF frequency and said second RF frequency.

16. An oral care device comprising:

a brush head;

a motor for driving the brush head with a vibratory motion with a vibration frequency;

a field generator, comprising one or more conductive elements, and adapted to generate an electric field in a mouth of a user, responsive to an input control signal; and a controller adapted to generate the input control signal, to control generation of the electric field, wherein the electric field is for imparting a force upon particles forming a biofilm to be removed by the oral care device, or upon cleaning agent particles, wherein the controller is adapted to generate a cyclic control signal for intermittent generation of an electric field at a first RF frequency, wherein the frequency of the cyclic control signal is equal to the vibration frequency or a sub-harmonic of the vibration frequency.

* * * * *